United States Patent
Yasuda et al.

(10) Patent No.: US 8,410,175 B2
(45) Date of Patent: Apr. 2, 2013

(54) ANTICANCER EFFECT ENHANCER

(75) Inventors: Hiroyasu Yasuda, Miyagi (JP); Mutsuo Yamaya, Miyagi (JP); Katsutoshi Nakayama, Miyagi (JP); Hidetada Sasaki, Miyagi (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/318,061

(22) Filed: Dec. 22, 2008

(65) Prior Publication Data

US 2009/0137683 A1 May 28, 2009

Related U.S. Application Data

(62) Division of application No. 11/628,943, filed as application No. PCT/JP2005/011078 on Jun. 10, 2005, now abandoned.

(30) Foreign Application Priority Data

Jun. 10, 2004 (JP) ................................ 2004-173174

(51) Int. Cl.
  *A61K 31/21* (2006.01)
  *A61K 33/00* (2006.01)
  *A61P 35/04* (2006.01)

(52) U.S. Cl. ........ 514/645; 514/221; 514/102; 424/718; 424/649; 424/600

(58) Field of Classification Search .................. 514/645, 514/221, 102; 424/718, 649, 600
See application file for complete search history.

(56) References Cited

U.S. PATENT DOCUMENTS

| | | | |
|---|---|---|---|
| 6,444,638 B2 * | 9/2002 | Schwartz et al. | 514/1 |
| 2002/0173538 A1 * | 11/2002 | Shiao | 514/449 |
| 2003/0215528 A1 * | 11/2003 | Graham et al. | 424/718 |

FOREIGN PATENT DOCUMENTS

| JP | 2004-508279 | 3/2004 |
|---|---|---|
| WO | WO03/074082 A1 | 9/2003 |

OTHER PUBLICATIONS

Calabresi et al (Goodman & Gilman's, Pharmacological basis of Therapeutics, 9th edition, 1995, pp. 1226-1229.*
Matthews, N.E. et al.;"Nitric oxide-mediated regulation of chemosensitivity in cancer cells;" J. Nat'l. Cancer Inst; vol. 93, No. 24, pp. 1879-1885 (2001).
Jordan, B.F., et al. "Changes in tumor oxygenation/perfusion induced by the NO donor, Isosorbide dinitrate, in comparison with carbogen: monitoring by EPR and MRI;" Int. J. Radiation Oncology Biol. Phys.; vol. 48, No. 2, pp. 565-570 (2000).
Liang, B.C.; "Effects of hypoxia on drug resistance phenotype and genotype in human glioma cell lines;" Journal of Neuro-Oncol.;vol. 29, p. 149-155 (1996).
Sanna, K. et al.; "Hypoxia-induced resistance to doxorubicin and methotrexate in human melanoma cell lines in vitro;" Int. J. Cancer; vol. 58, pp. 258-262 (1994).

(Continued)

*Primary Examiner* — Savitha Rao
(74) *Attorney, Agent, or Firm* — Kratz, Quintos & Hanson, LLP

(57) ABSTRACT

An object of the present invention is to provide an enhancing agent for effect of anticancer agent for achieving an excellent therapeutic effect on cancer. The enhancing agent for effect of anticancer agent according to the present invention which is a solving means therefor is characterized in that a nitric oxide donor is an effective ingredient. In accordance with the present invention, an excellent therapeutic effect is able to be achieved on non-small cell lung cancer which is still in such a state that no effective therapeutic method has been established yet for a progressive cancer which is not operable and is one of cancers where chemotherapy is most difficult to apply.

5 Claims, 3 Drawing Sheets

OTHER PUBLICATIONS

Gallo, O. et al.; "Role of nitric oxide in angiogenesis and tumor progression in head and neck cancer;" J. Natl. Cancer Inst.; vol. 90, No. 8, pp. 587-596 (1998).

Edwards, P. et al.; Tumor cell nitric oxide inhibits cell growth in vitro, but stimulates tumorigenesis and experimental lung metastasis in vivo; Journal of Surg. Res.; vol. 63, pp. 49-52 (1996).

Ambs, S. et al.; "p53 and vascular endothelial growth factor regulate tumour growth of NOS2-expressing human carcinoma cells;" Nature Med.; vol. 4, No. 12, pp. 1371-1376 (1998).

Jenkins, D.C. et al.; "Roles of Nitric Oxide in Tumor Growth;" Proc. Natl. Acad. Sci. USA.; vol. 92, pp. 4392-4396 (1995).

Lala, P.K. et al.; "Role of nitric oxide in carciogenesis and tumour progression;" Lancet Oncol; vol. 2, pp. 149-156 (2001).

Pipili-Synetos E. et al.; "Inhibition of Angiogenesis, tumour growth and metastasis by the NO-releasing vasodilators, isosorbide mononitrate and dinitrate;" British Journal of Pharmacology, vol. 116, No. 2, pp. 1829-1834 (1995).

Jordan, B.F. et al.; "Potentiation of radiation-induced regrowth delay by isosorbide dinitrate in FSAII murine tumors;" International Journal of Cancer, vol. 103, No. 1, pp. 138-141 (2003).

International Search Report for PCT/JP2005/011078 together with International Preliminary Report and Reply.

David A. Wink et al, Nitric Oxide and some Nitric Oxide Donor Compounds Enhance the Cytotoxicity of Cisplatin, Nitric Oxide: Biology and Chemistry, vol., No. 1, pp. 88-94, (1997).

K.P. Konovalova et al., Nitric oxide donor increases the efficeincy of cytostatic therapy and retards the development of drug resistance, Nitric Oxide, vol. 8, pp. 59-64, (2003).

Hiroyasu Yasuda et al.: "Randomized Phase II Trial Comparing Nitroglycerin Plus Vinorelbine and Cisplatin With Vinorelbine and Cisplatin Alone in Previously Untreated State IIIB/IV Non-Small-Cell Lung Cancer", *Journal of Clinical Oncology*, vol. 24, No. 4, Feb. 1, 2008, pp. 688-694.

\* cited by examiner

*p<0.05 vs N+CTX

*p<0.05 vs N+CTX

ANTICANCER EFFECT ENHANCER

CROSS REFERENCE TO RELATED APPLICATION

This application is a Divisional Application of prior application Ser. No. 11/628,943, filed on Feb. 23, 2007, now abandoned which was a §371 National Stage Application of PCT/JP05/11078, filed on Jun. 10, 2005, the previous applications being hereby incorporated by reference.

TECHNICAL FIELD

The present invention relates to an enhancing agent for effect of anticancer agent for achieving an excellent therapeutic effect on cancer.

BACKGROUND ART

It has been well known that, as a result of vigorous research and development of anticancer agents for many years, various kinds of anticancer agents are now being used in chemotherapy to various types of cancer and therapeutic effect is achieved thereby. However, it has been also known that there is no anticancer agent which is effective on all types of cancer and there is a limitation for the therapeutic effect of anticancer agent on cancer.

As one of the causes for the limitation in the therapeutic effect on cancer by anticancer agent, it has been reported that hypoxic condition inside the solid cancer participates in resistance to its therapy. For example, in Non-Patent Document 1 (Matthews N E, Adams M A, Maxwell L R, Gofton T E, Graham C H. Nitric oxide-mediated regulation of chemosensitivity in cancer cells. *J. Natl. Cancer Inst.,* 2001; 93: 187-1885), it is shown that, in experiments where several kinds of cancer cell lines are actually used, hypoxic condition promotes the resistance of cancer cells to anticancer agent. In this document, it is made clear that, when an anticancer agent is mixed with culture medium of cancer cell lines, the surviving rate is as high as two-fold or more even if the cancer cells are directly exposed to the anticancer agent as compared with the case where they are exposed in normoxic condition provided that they are exposed in hypoxic condition. It is also made clear that hypoxic condition suppresses an endogenous production of nitric oxide (NO) whereby it enhances the resistance of the cancer cells to anticancer agent and that administration of an exogenous NO donor improves the resistance to anticancer agent by hypoxic condition. Besides that, in Non-Patent Document 2 (Jordan B F, Misson P D, Demeure R, Baudelet C, Beghein N, Gallez B. Changes In tumor oxygenation/perfusion induced by the NO donor, Isosorbide dinitrate, In comparison with carbogen: monitoring by EPR and MRI. *Int. J. Radiation Oncology Biol. Phys.,* 2000; 48: 565-570), it is suggested that isosorbide dinitrate which is a NO donor improves oxygen pressure inside the cancer due to an increase in blood flow. In Non-Patent Document 3 (Liang B C. Effects of hypoxia on drug resistance phenotype and genotype in human glioma cell lines. *J. Neurooncol.,* 1996; 29: 149-155), it is made clear that, when glioma cell line is placed in hypoxic condition, it shows resistance to anticancer agent. In Non-Patent Document 4 (Sanna N, Rofstad E K. Hypoxia-induced resistance to doxorubicin and methotrexate in human melanoma cell lines in vitro. *Int. J. Cancer,* 1994; 58: 258-262), it is made clear that, when human melanoma cell line is placed in hypoxic condition, it shows resistance to anticancer agent. Thus, according to those reports, even when anticancer agent is merely distributed in large quantities in cancer cells, death of cancer cells is not accelerated unless hypoxic condition in tumor tissues is improved. Non-Patent Document 1 and Non-Patent Document 2 suggest that a NO donor is able to effectively function in improvement of hypoxic condition inside the solid cancer.

However, in any of the reports, it is not proved that NO actually enhances the therapeutic effect of anticancer agent on cancer in human clinical medicine. Rather, there are many reports which suggest that NO has an action of increasing the tumor size and promoting its progress. For example, in Non-Patent Document 5 (Gallo O, Masini E, Morbidelli L, Franchi A, et al. Role of nitric oxide in angiogenesis in head and neck cancer. *J. Natl. Cancer Inst.,* 1998; 90: 587-596), a NO synthase (NOS) participating in NO production in tissue preparation of human head and neck cancer is investigated and it is shown that, in advanced cancer cases accompanied by metastasis to lymph node, expressed amount of NOS is high and blood vessel density in lymph node is high in a group where metastasis to lymph node is positive. In this document, an investigation using cornea of rabbit is also conducted for tumor angiogenetic effect of NO on cancer tissues prepared from human head and neck cancer cases. According to that, it is suggested that, in a group to which L-NAME which is a NOS inhibitor is administered, tumor angiogenesis is significantly little and progress of cancer is suppressed as compared with a control group and it is shown that NO has a promoting action for increase and progress of cancer tissues via tumor angiogenesis. In Non-Patent Document 6 (Edwards P, Cendab J C, Topping D B, Moldawer L L, Mackay S, Copeland E M, Lind D S. Tumor cell nitric oxide inhibits cell growth in vitro, but stimulates tumorigenesis and experimental lung metastasis in vivo. *J. Surg. Res.,* 1996; 63: 49-52), it is shown that, when an experiment using cultured cells where NO production is promoted by stimulation of LPS/IFN-γ using EMT-6 cells (breast cancer cell line of mice) is conducted, growth of tumor cells is suppressed while, when the same cells are transplanted to BALB/c mouse and stimulated by LPS/IFN-γ, tumor tissues and lung metastasis increased to an extent of two-fold as compared with a control group and that experimental results are entirely opposite between an experiment using cultured cells (in vitro experiment) and an animal experiment (in vivo experiment). In the Non-Patent Document 7 (Ambs S, Merriam W G, Ogunfusika M O, Bennett W P, Ishibe N, et al. p53 and vascular endothelial growth factor regulate tumor growth of NOS2-expressing human carcinoma cells. *Nature Med.,* 1998; 4: 1371-1376), an influence of NO on angiogenesis and cancer progress is investigated in an animal experiment where a human cancer cell line into which NOS gene is introduced so as to conduct a NO synthesis in a constant manner is transplanted to nude mice having no thymus. Here, relation to the presence/absence of an activity of cancer suppressive gene p53 is investigated and it is shown that, in tumor tissues where cancer cell line having a p53 activity (wild type p53) is transplanted to nude mice, an endogenous NO suppresses the growth of tumor cells while, in tumor tissues where cancer cell line having poor p53 activity (mutant p53) is transplanted to nude mice, the endogenous NO promotes VEGF expression and angiogenesis, and promotes the growth of tumor cells. In Non-Patent Document 8 (D C Jenkins, I G Charles, L L Thomsen, D W Moss, L S Holmes, S A Baylis, P Rhodes, K Westmore, P C Emson, S Moncada. Roles of Nitric Oxide in Tumor Growth. *Proc. Natl. Acad. Sci. USA,* 1995; 92: 4392-4396), it is shown that, inhuman breast cancer and cancer in a gynecologic field, NO production and cancer growth show a positive correlation. In Non-Patent Document 9 (Lala P K, Chakraborty C. Role of nitric oxide in carcinogenesis and tumour progression. *Lan-*

*cet Oncol.*, 2001; 2: 149-156), it is shown that NOS of a derived type participates in mutation of p53 of tumor of colon, lung and throat and that NO stimulates the growth of tumor via activation of cyclooxygenase-2 (COX-2). Thus, according to those reports, it is strongly suggested that, in establishing a therapy of cancer by anticancer agent in human clinical medicine, the use of NO has a possibility of causing adverse effects to patients such as increase or progress of cancer.

As mentioned above, with regard to an action of NO to cancer, each of the reports mentioning it participates in the direction of suppressing the cancer and the reports mentioning it participates in the direction of worsening the cancer are present in large numbers being supported by scientific proof and a scientific evaluation therefor is in a chaotic state. Moreover, as shown in Non-Patent Document 6, it is never rare that the experimental results are entirely contrary between an experiment using cultured cells and an animal experiment. In view of such circumstances, in Non-Patent Document 1 for example, it is shown that resistance of cancer cell line to anticancer agent induced by hypoxic condition is improved by a NO donor in an experiment using cultured cells and, although such a finding will be surely valuable for showing one direction for future research, it is not possible to conclude from such a finding that a NO donor has an action of shrinking the cancer tissues or an action of enhancing the effect of anticancer agent. So, it is all the more that, in human clinical medicine, a conclusion that a NO donor enhances the effect of anticancer agent is unable to be done and should not be done.

In Patent Document 1 (JP 2004-508279 A), there is proposed a method of administering a NO donor as a potassium channel activator as a method for a selective transfer of anticancer agent to cancer where permeability of blood vessel or sending blood to cancer cells to anticancer agent is enhanced. However, issue of a jumped conclusion that a NO donor enhances the effect of anticancer agent only by appealing an increase in transition of an anticancer agent to tumor tissues by an increase in permeability through blood vessel without actual confirmation of enhancement of NO donor in the action of anticancer agent to cancer tissues even in animal experiment is not convincing at all under the present status where scientific evaluation for the action of NO to cancer is in chaos as mentioned above. Patent Document 1 is far behind the conclusion that a NO donor results in enhancement of effect of anticancer agent in actual human clinical medicine. In fact, with regard to data showing that improvement in therapeutic effect for cancer was able to be achieved by that method, no data is available even for animal experiment in Patent Document 1.

Therefore, an object of the present invention is to provide an enhancing agent for effect of anticancer agent for achieving an excellent therapeutic effect on cancer.

DISCLOSURE OF THE INVENTION

Under the circumstance where, even in animal experiments, no conclusion is issued what effect is available by administration of a NO donor to cancer tissues, the present inventors have at this time found that a NO donor dramatically improves the therapeutic effect of an anticancer agent on non-small cell lung cancer which is believed to be one of the most difficult cancers for chemotherapy. One of the backgrounds therefor is a retrospective clinical research in patients with either angina pectoris or old myocardial infarction treated with a NO donor. That is because there is a ground of a data analysis where response rate by chemotherapy is quite significantly higher in a group suffering from advanced non-small cell lung cancer and receiving a chemotherapy (MVP therapy) (group where NO is used together; age: 67±8; male ratio: 80%) than a group using no NO donor and receiving the same MVP therapy (control group; age: 65±9; male ratio: 76%) where odds ratio=30.6, 95% CI 3.5-270.4, p<0.0001, Chi-square test. In the data, response rate of the group where NO was used together was 90% (CR: 20%, 2/10; PR: 70%, 7/10; NC: 10%, 1/10; PD: 0%, 0/10) while response rate of the control group was 23% (CR: 0%, 0/44; PR: 23%, 10/44; NC: 50%, 22/44; PD: 27%, 12/44) (With regard to the method for judgment, refer to the Examples which will be mentioned later).

The present invention has been achieved on the basis of the above-mentioned finding, and according to a first aspect and feature of the present invention, there is provided an enhancing agent for effect of anticancer agent which is characterized in that a NO donor is an effective ingredient.

According to a second aspect and feature of the present invention, in addition to the first feature, the cancer which is an object for the treatment is solid cancer.

According to a third aspect and feature of the present invention, in addition to the second feature, the solid cancer is non-small cell lung cancer.

According to a fourth aspect and feature of the present invention, in addition to the first feature, the NO donor is an organic nitrate compound.

In accordance with the present invention, it is possible to provide an enhancing agent for effect of anticancer agent for achieving an excellent therapeutic effect on cancer.

BEST MODE FOR CARRYING OUT THE INVENTION

Figure 1:
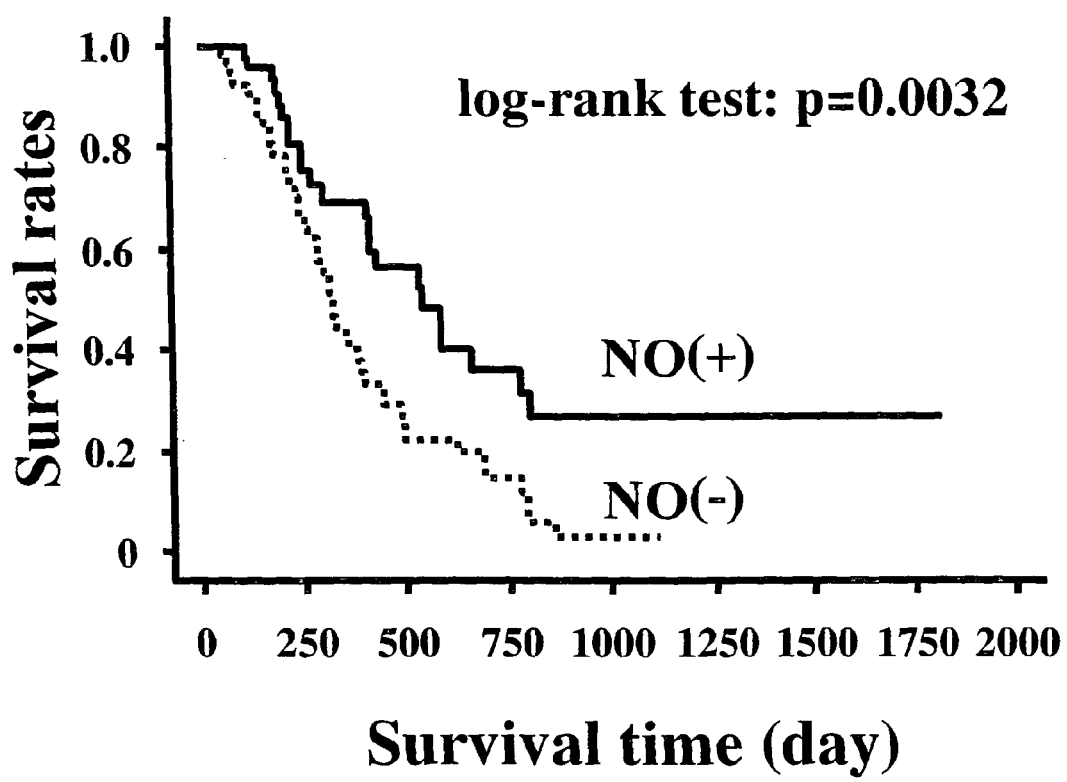
FIG. 1 is a drawing which shows survival rate curves in patients with advanced non-small cell lung cancer treated with NO donors {NO(+)} (solid line) and without NO donors {NO(−)} (dotted line) during chemotherapy. The P value was calculated by the log-rank test.

In the present invention, a nitric oxide (NO) donor means an agent which is able to release NO under a physiological condition. For example, organic nitrate compounds which are nitric esters of monohydric or polyhydric alcohol are included in this category. Their representative examples are nitroglycerin (NTG), pentaerythrityl tetranitrate (PETN), isosorbide dinitrate (ISDN) and isosorbide mononitrate (ISMN).

There is no particular limitation for an anticancer agent which is used in chemotherapy where effect is enhanced by the concomitant use of a NO donor and its examples are antimetabolites exemplified by 5-fluorouracil, methotrexate, doxifluridine, tegafur, cytarabine and gemcitabine; alkylating agents exemplified by cyclophosphamide, ifosfamide, thiotepa, carboquone and nimustine hydrochloride; anticancer antibiotics exemplified by mitomycin, doxorubicin hydrochloride, amurubicin hydrochloride, pirarubicin hydrochloride, epirubicin hydrochloride, aclarubicin hydrochloride, mitoxantrone hydrochloride, bleomycin hydrochloride and peplomycin sulfate; microtubule-acting agents exemplified by docetaxel, paclitaxel, vincristine, vindesine and vinorelbine; platinum-based agents exemplified by cisplatin, carboplatin and nedaplatin; topoisomerase inhibitors exemplified by irinotecan and nogitecan hydrochloride; and alkaloidal anticancer agents exemplified by etoposide.

With regard to a NO donor, an example is that its administration is started to a patient who is subjected to a standard chemotherapy from 5 to 2 days before the start of the chemotherapy (preferably, 3 days before), the administration is continued during the period of chemotherapy and, at the stage where chemotherapy is finished, the administration is stopped. Although there is no particular limitation for the dosage form of the NO donor, it is preferred to be an oral preparation or a subcutaneous preparation where control of concentration in blood is easy when risk of expression of resistance is taken into consideration. The dose may be in accordance with a dose in the treatment of angina pectoris which is an inherent use of a NO donor. To be more specific, when nitroglycerin is used, administration may be in a dose of 1 to 50 mg/day (being divided into two administrations a day) in the case of oral administration by means of tablets or the like and 1 to 50 mg/day (applied once daily) in the case of transdermally administration by means of plaster or the like. When isosorbide dinitrate is used, administration may be in a dose of 10 to 100 mg/day (being divided into two administrations a day) in the case of oral administration and 10 to 100 mg/day (applied once daily) in the case of transdermally administration. Incidentally, the above description does not deny the administration of a NO donor in a form of a combined preparation with an anticancer agent.

There is no particular limitation for the cancer which is an object of the treatment in the present invention but any cancer may be applied so far as it is a cancer which is able to be an object of chemotherapy. Specific examples thereof are solid cancer such as head and neck cancer, stomach cancer, colon cancer, rectum cancer, hepatic cancer, gall and bile duct cancer, pancreatic cancer, lung cancer, breast cancer, bladder cancer, prostate cancer and uterine neck cancer, and blood cancer such as malignant lymphoma and leukemia.

EXAMPLES

The present invention shall be described as following. Any limitations in interpretation will not arise according to following documents.

Example 1

A Study of the Effect of Concomitant Use of NO Donors with Anticancer Agents on Response to Chemotherapy in Patients with Advanced Non-Small Cell Lung Cancer in a Prospective Randomised Controlled Trial Characteristics of the Subjects Sixty five patients with inoperable advanced non-small cell lung cancer (NSCLC) fit the following five criteria and were recruited in this study: (a) stage IIIB or stage IV; (b) no prior chemotherapy or radiotherapy; (c) good performance status: a performance status of 0-2 according to the Eastern Cooperative Oncology Group (ECOG) scale; (d) without brain metastasis; (e) adequate renal function, hepatic function, hematological function and cardiac function.

Of the 65 patients with advanced NSCLC, 31 patients had squamous cell carcinoma (19 patients in stage IIIB and 12 patients in stage IV), 29 patients had adenocarcinoma (9 patients in stage IIIB and 20 patients in stage IV), 5 patients had large cell carcinoma (4 patients in stage IIIB and 1 patients in stage 1V), and all patients were randomly assigned to receive anticancer agents with or without NO donors during chemotherapy in a prospective cohort study.

Thirty two of the 65 patients with advanced NSCLC were treated with chemotherapy with a NO donor (transdermally applied nitroglycerin, Nitroderm TTS®, 25 mg/body daily, or orally administered isosorbide dinitrate, Nitrol R®, 40 mg/body daily divided into two administrations, between 3 days before the start of each course of chemotherapy and the finish of administration of anticancer agents). In group treated with a NO donor, 21 of 32 patients were treated with MVP, cisplatin (CDDP) plus vinorelbine (VNR) plus mitomycin (CDDP 80 mg/m$^2$ day 1, VNR 25 mg/m$^2$ day 1 and 8, mitomycin 8 mg/m$^2$ day 1, in every 21 days), 6 of 32 patients were treated with CDDP plus docetaxel (DOC) (CDDP 80 mg/m$^2$ day 1, DOC; 75 mg/m$^2$ day 1, in every 21 days), and 5 of 32 patients were treated with CDDP plus VNR (CDDP 80 mg/m$^2$ day 1, VNR 25 mg/m$^2$ day 1 and 8, in every 21 days). Another 33 of the 65 patients with advanced NSCLC were treated with chemotherapy without a NO donor. In group treated without a NO donor, 18 of 33 patients were treated with MVP, CDDP plus VNR plus mitomycin (CDDP 80 mg/m$^2$ day 1, VNR 25 mg/m$^2$ day 1 and 8, mitomycin 8 mg/m$^2$ day 1, in every 21 days), 8 of 33 patients were treated with CDDP plus DOC (CDDP 80 mg/m$^2$ day 1, DOC; 75 mg/m$^2$ day 1, in every 21 days), and 7 of 33 patients were treated with CDDP plus VNR (CDDP 80 mg/m$^2$ day 1, VNR 25 mg/m$^2$ day 1 and 8, in every 21 days). Characteristics of the subjects in arm A and arm B are shown in Table 1.

TABLE 1

Characteristics of patients with advanced non-small cell lung cancer.

| Characteristics | With NO mimetics (Arm A, n = 32) | Without NO mimetics (Arm B, n = 33) | p value |
| --- | --- | --- | --- |
| Age (year) | | | |
| Median | 68 | 67 | 0.2615* |
| Range | 41-83 | 48-84 | |
| Gender (No. of patients) | | | |
| Male | 29 | 24 | 0.063 |
| Female | 3 | 9 | |
| Performance Status (No. of patients) | | | |
| 0 | 23 | 23 | 0.8469 |
| 1 | 6 | 6 | 0.9529 |
| 2 | 3 | 4 | 0.721 |
| Brinkman Index (pack-year) | | | |
| Median | 49 | 47 | 0.6334* |
| Range | 0-120 | 0-125 | |

TABLE 1-continued

Characteristics of patients with advanced non-small cell lung cancer.

| Characteristics | With NO mimetics (Arm A, n = 32) | Without NO mimetics (Arm B, n = 33) | p value |
|---|---|---|---|
| Cell type (No. of patients) | | | |
| Squamous cell | 18 | 13 | 0.1737 |
| Adenocarcinoma | 10 | 19 | 0.0328 |
| Large cell | 4 | 1 | 0.1520 |
| Stage (No. of patients) | | | |
| III B | 17 | 15 | 0.5363 |
| IV | 15 | 18 | |
| Chemotherapy (No. of patients) | | | |
| MVP | 21 | 18 | 0.362 |
| CDDP + DOC | 6 | 8 | 0.5902 |
| CDDP + VNR | 5 | 7 | 0.5616 |

MVP = mitomycin C + vinorelbine + cisplatin,
CDDP = cisplatin,
DOC = docetaxel,
VNR = vinorelbine.
Two factors marked * was statistically assessed with the Mann-Whitney U test.
Other factors was assessed with the Chi-square test.

Methods

NO donors were used between 3 days before the start of each course of chemotherapy and the finish of administration of anticancer agents. To assess the effects of NO donors on the chemosensitivity, we compared the tumor sizes with the chest computed tomography (CT) scan before and after treatment with anticancer agents. The nodal staging of lung cancer was determined using a CT scan and a Gallium-67 citrate scintigram of the chest. The metastasis in the brain, the abdomen and the bone was determined using a CT scan of the brain and abdomen, and a Technetium-99m scintigram of the bone. Complete response (CR) was defined as the disappearance of all known disease determined by two observations not less than two weeks apart. Partial response (PR) was defined as a 50% or more decrease in the total tumor size of those lesions measured during two observations not less than four weeks apart. No change (NC) was defined as cases where a 50% decrease in the total tumor size could not be established, and also there was not a 25% or greater increase in the size of one or more measurable lesions. Progressive disease (PD) was defined as a 25% or greater increase in the size of one or more measurable lesions or the appearance of new lesions. The patients were categorized as responders when they experienced either PR or CPR. The patients with NC or PD were categorized as non-responders. Response rate to chemotherapy was calculated by the number of responders divided by the number of responders plus non-responders. Survival was calculated from the date of the first day of first cycle of the chemotherapy to the date of death or a cutoff date for patients alive at the time of closure of the data set.

The factors associated with the response to the chemotherapy were assessed by univariate analysis (Chi-square test) and multivariate analysis (Logistic regression analysis). Cox regression analysis was performed to assess the prognostic significance of the variables. We analyzed the survival rate with the Kaplan-Meire method, and the p-value of survival curves between patients treated with anticancer agents and NO donors and patients treated with anticancer agents alone with the Log-rank test. Significance was accepted at $p<0.05$.

Explanation of Technical Term (No. 1)

ECOG Performance Status (PS):

| Grade | ECOG |
|---|---|
| 0 | Fully active, able to carry on all pre-disease performance without restriction |
| 1 | Restricted in physically strenuous activity but ambulatory and able to carry out work of a light or sedentary nature, e.g., light house work, office work |
| 2 | Ambulatory and capable of all selfcare but unable to carry out any work activities. Up and about more than 50% of waking hours |
| 3 | Capable of only limited selfcare, confined to bed or chair more than 50% of waking hours |
| 4 | Completely disabled. Cannot carry on any selfcare. Totally confined to bed or chair |
| 5 | Dead |

* Am J Clin Oncol 5: 649-655, 1982.

Explanation of Technical Term (No. 2)

Brinkman Index: a smoking history calculated by multiplying the number of cigarettes consumed a day (number of packages of cigarettes) by smoking duration (years).

Results

Characteristics of the subjects in responders and non-responders are shown in Table 2 and Table 3. Survival curves for the group treated with NO donors and the group treated without NO donors calculated by Kaplan-Meier analysis are shown in FIG. 1.

TABLE 2

Analysis of risk factors for chemosensitivity assessed by multivariate analysis.

| Characteristics | PR + CR (Responder) (n = 39) | NC + PD (Non-responder) (n = 26) | Multivariate analysis p value |
|---|---|---|---|
| Age (year) | | | |
| 65≧ | 30 (67%) | 15 (33%) | 0.792 |
| 65< | 9 (45%) | 11 (55%) | |
| Gender (No. of patients) | | | |
| Male | 35 (66%) | 18 (34%) | 0.438 |
| Female | 4 (33%) | 8 (67%) | |
| Performance Status (No. of patients) | | | |
| 0 | 28 (61%) | 18 (39%) | 0.927 |
| 1 | 6 (50%) | 6 (50%) | |
| 2 | 5 (71%) | 2 (29%) | |
| Brinkman Index (pack-year) | | | |
| 50≧ | 20 (74%) | 7 (26%) | 0.899 |
| 50< | 19 (50%) | 19 (50%) | |
| Cell type (No. of patients) | | | |
| Squamous cell | 26 (84%) | 5 (16%) | 0.011 |
| Adenocarcinoma | 10 (34%) | 19 (66%) | — |
| Large cell | 3 (60%) | 2 (40%) | 0.948 |
| Staging (No. of patients) | | | |
| III B | 24 (75%) | 8 (25%) | 0.098 |
| IV | 15 (45%) | 18 (55%) | |
| Chemotherapy (No. of patients) | | | |
| MVP | 26 (67%) | 13 (33%) | 0.199 |
| CDDP + DOC | 7 (50%) | 7 (50%) | 0.358 |
| CDDP + VNR | 6 (50%) | 6 (50%) | — |
| Vital Capacity | | | |

TABLE 2-continued

Analysis of risk factors for chemosensitivity assessed by multivariate analysis.

| Characteristics | PR + CR (Responder) (n = 39) | NC + PD (Non-responder) (n = 26) | Multivariate analysis p value |
|---|---|---|---|
| (% predicted) | | | |
| <80% | 7 (78%) | 2 (22%) | 0.724 |
| ≧80% | 32 (57%) | 24 (43%) | |
| Forced Expiratory Volume in 1 second (% predicted) | | | |
| <70% | 18 (72%) | 7 (28%) | 0.299 |
| ≧70% | 21 (53%) | 19 (47%) | |
| Use of NO Mimetics (No. of patients) | | | |
| yes | 26 (81%) | 6 (19%) | 0.007 |
| No | 13 (39%) | 20 (61%) | |
| Use of vasodilator except for NO mimetics (No. of patients) | | | |
| yes | 18 (69%) | 8 (31%) | 0.246 |
| No | 21 (54%) | 18 (46%) | |

CR = complete response,
PR = partial response,
NC = no change,
PD = progressive disease,
NO = nitric oxide,
MVP = mitomycin C + vinorelbine + cisplatin,
CDDP = cisplatin,
DOC = docetaxel,
VNR = vinorelbine.
Multivariate analysis was performed with Logistic regression analysis.

TABLE 3

The relationship between the use of NO donors and anticancer drugs and chemosensitivity in a clinical research

| | Anticancer drugs | Responder; CR + PR (Number) | | Non-responder; NC + PD (Number) | |
|---|---|---|---|---|---|
| The use of NO donors (+) | MVP | 17 | 26 | 4 | 6 |
| | CDDP + DOC | 5 | | 1 | |
| | CDDP + VNR | 4 | | 1 | |
| The use of NO donors (−) | MVP | 9 | 13 | 9 | 20 |
| | CDDP + DOC | 2 | | 6 | |
| | CDDP + VNR | 2 | | 5 | |

CR = complete response,
PR = partial response,
NC = no change,
PD = progressive disease,
NO = nitric oxide,
MVP = mitomycin C + vinorelbine + cisplatin,
CDDP = cisplatin,
DOC = docetaxel,
VNR = vinorelbine.

There were no statistical significances between patients with advanced NSCLC treated with anticancer agents and NO donors and patients treated with anticancer agents alone in age, gender, performance status, smoking history, stage of lung cancer and protocol of chemotherapy (Table 1). Remarkable strong effects of the use of NO donors combined with anticancer agents on response rate to chemotherapy in patients with advanced NSCLC were recognized as shown in Table 2 and Table 3. Response rate in patients treated with NO donors during chemotherapy (81%, 26 of 32 patients) was significantly higher than that in patients treated without NO donors (39%, 13 of patients) (Odds ratio=6.7, 95% CI 2.2-20.7, p=0.0006, Chi-square test) (Table 2). The use of NO donors (p<0.01) was significantly associated with a positive response to anticancer agents in patients with advanced NSCLC (Logistic regression analysis) (Table 2). Kaplan-Meier analysis showed that the survival in patients treated with anticancer agents and NO donors was significantly longer than that in patients treated with anticancer agents alone (p<0.05) (Log-rank test). These results (Table 2 and Table 3) suggest that the use of NO donors, such as nitroglycerin and isosorbide dinitrate, may improve the response to chemotherapy in patients with stage IIIB or stage 1V of advanced NSCLC.

Conclusions

The use of NO donors combined with anticancer agents turned out to have a great additional effect on the improvement of response rate to chemotherapy and overall survival in patients with advanced NSCLC compared with those in patients treated with anticancer agents without NO donors.

Treating advanced NSCLC, squamous cell carcinoma, adenocarcinoma, and large cell carcinoma remains very difficult because advanced NSCLC is not operable and the response rate to anticancer agents even if the newest third-generation anticancer agents is very low. In contrast, the response rate to chemotherapy in small cell lung cancer is about 70-80% and is significantly higher than that in NSCLC. The number of patients with lung cancer has been increasing in most countries in the world year by year in contrast to the number or patients with gastric cancer. Furthermore, a large proportion of lung cancer consists of NSCLC. Therefore, a more effective new regimen in advanced NSCLC than currently exists should be established at once. On this point, the present invention may have a great significance on improving the response rate to not only NSCLC but other kinds of advanced solid cancer.

Example 2

Concomitant Use of a NO Donor, Nitroglycerin, Improves Chemosensitivity in Murine Lung Cancer Model Methods Murine Lewis lung carcinoma (LLC) cells, lung adenocarcinoma cells, were obtained from the Tohoku University Cell Resource Center for Biomedical Research and were incubated with DMEM plus 10% fetal bovine serum until cell proliferation was sufficient to perform the experiments. The LLC cells were adjusted to concentrations of $2 \times 10^5$ cells/100 µl with phosphate buffer saline (PBS), and were inoculated Six-week-old male C57BL6 mice purchased from Charles River Japan, Inc. (Tokyo, Japan) and Clea Japan, Inc. (Tokyo, Japan) subcutaneously ($2 \times 10^5$ cells/100 µl/mouse) at the right hypochondrium. Mice were maintained under specific-pathogen-free conditions, and provided with sterile food and water. When transplanted tumors grew to approximately 100 mm$^3$ in tumor volume, animals were equally divided into four groups (Control group, n=6; C, NO donor group, n=6; N, Chemotherapy group, n=6; CTX, and NO plus chemotherapy group, n=6; N+CTX). Tumor volume was calculated as 0.5× {tumor length (mm)}×{tumor width (mm)}$^2$. In the control group, 100 µl of PBS was administered by intra-peritoneal injection (i.p.) four times a week (once on Sunday, once on Monday, once on Wednesday, once on Thursday) and 100 µl of PBS was further administered by intravenous injection (i.v.) 30 minutes after the i.p. twice a week (once on Monday and once on Thursday) into the C57BL6 mice. The experiments were performed for two weeks. In the NO donor group, 100 µl of 0.02 mg/kg nitroglycerin diluted with PBS was administered i.p. into the mice four times a week (once on Sunday, once on Monday, once on Wednesday, once on Thursday) and 100 μl of PBS was administered i.v. into the mice 30 minutes after the nitroglycerin solution i.p. twice a week (once on Monday and once on Thursday). The experiments were performed for two weeks. In the chemotherapy group, 100 μl of PBS was administered i.p. into the mice four times a week (once on Sunday, once on Monday, once on Wednesday, once on Thursday) and 100 μl of 3.5 mg/kg cisplatin solution dissolved in PBS was administered i.v. into the mice 30 minutes after the PBS i.p. twice a week (once on Monday and once on Thursday). The experiments were performed for two weeks. In the NO plus chemotherapy group, 100 μl of 0.02 mg/kg nitroglycerin diluted with PBS was administered i.p. into the mice four times a week (once on Sunday, once on Monday, once on Wednesday, once on Thursday) and 100 μl of 3.5 mg/kg cisplatin solution dissolved in PBS was administered i.v. into the mice 30 minutes after the nitroglycerin solution i.p. twice a week (once on Monday and once on Thursday). The experiments were performed for two weeks. Cisplatin and nitroglycerin were obtained from Nippon Kayaku Co., Ltd (Tokyo, Japan). Measurements of murine tumor volume and mice body weight were performed every two days after the start of injections into mice.

Results

Figure 2:
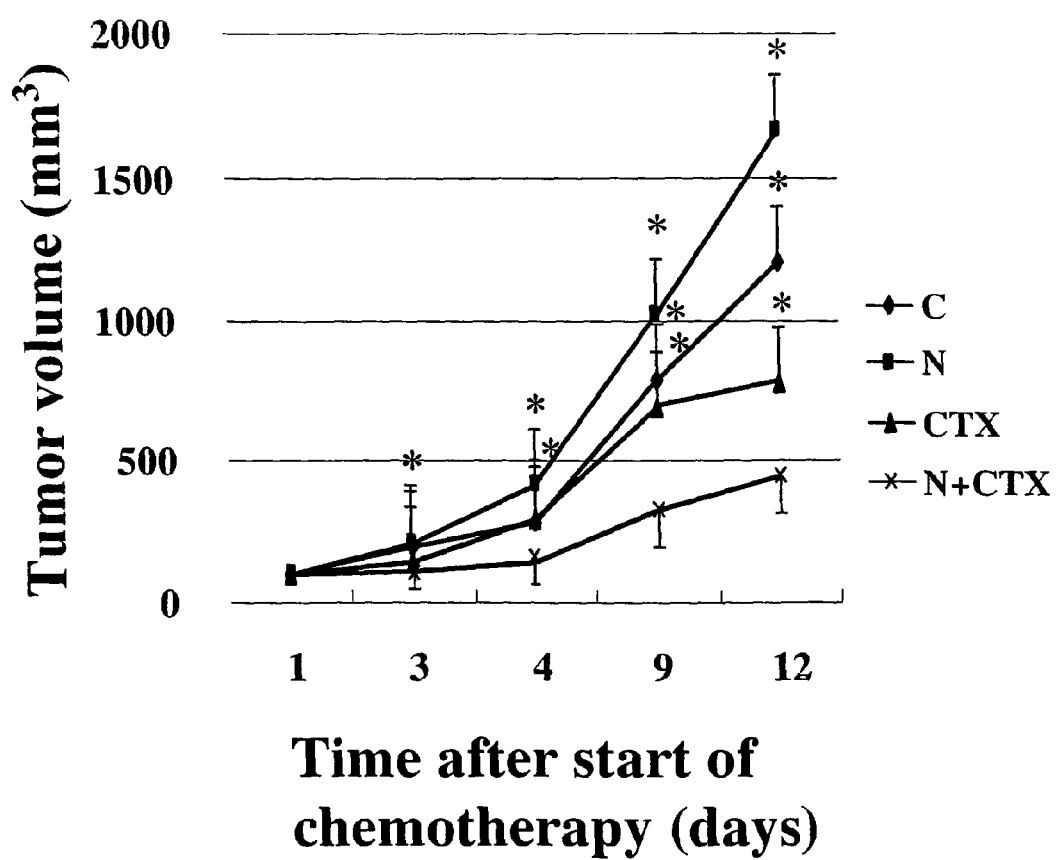
FIG. 2 shows the tumor volume growth curves in lung cancer model (Murine Lewis lung carcinoma; LLC cells) in C57BL6 mice (Control group, n=6; C, NO donor group, n=6; N, Chemotherapy group, n=6; CTX, and NC) plus chemotherapy group, n=6; N+CT-X). Tumor volume was calculated as $0.5 \times \{\text{tumor length (mm)}\} \therefore \{\text{tumor width (mm)}\}^2$. The = value was calculated by student t-test.

The tumor volume growth curve is shown in FIG. 2. Significant diminishing of murine tumor volume was observed after day 9 in the NO plus chemotherapy group compared with that in the chemotherapy group. On the other hand, the NO donor group as well as the control group showed rapid tumor growth compared with that in the chemotherapy group and the NO plus chemotherapy group.

These data suggest that the chance of a new commercial use of NO donors as an enhancing agent for effect of anticancer agents can be enlarged because of their excellent effect on the improvement of chemosensitivity especially in difficult solid cancers to treat with chemotherapy.

Example 3

Concomitant Use of a NO Donor, Nitroglycerin, Improves Chemosensitivity in Murine Colon Cancer Model Methods Colon 26 cells, murine colon cancer cells, were obtained from the Tohoku University Cell Resource Center for Biomedical Research and were incubated with RPMI 1640 plus 10% fetal bovine serum until cell proliferation was sufficient to perform the experiments. The colon 26 cells were adjusted to concentrations of $2\times10^5$ cells/100 μl with phosphate buffer saline (PBS), and were inoculated Six-week-old female BALB/c mice purchased from Charles River Japan, Inc. (Tokyo, Japan) and Clea Japan, Inc. (Tokyo, Japan) subcutanously ($2\times10^5$ cells/100 μl/mouse) at the right hypochondrium. Mice were maintained under specific-pathogen-free conditions, and provided with sterile food and water. When transplanted tumors grew to approximately 100 mm³ in tumor volume, animals were equally divided into four groups (Control group, n=6; C, NO donor group, n=6; N, Chemotherapy group, n=6; CTX, and NO plus chemotherapy group, n=6; N+CTX). Tumor volume was calculated as 0.5×{tumor length (mm)}×{tumor width (mm)}². In the control group, 100 μl of PBS was administered by intra-peritoneal injection (i.p.) four times a week (once on Sunday, once on Monday, once on Wednesday, once on Thursday) and 100 μl of PBS was further administered by intravenous injection (i.v.) 30 minutes after the i.p. twice a week (once on Monday and once on Thursday) into the BALB/c mice. The experiments were performed for two weeks. In the NO donor group, 100 μl of 0.02 mg/kg nitroglycerin diluted with PBS was administered i.p. into the mice four times a week (once on Sunday, once on Monday, once on Wednesday, once on Thursday) and 100 μl of PBS was administered i.v. into the mice 30 minutes after the nitroglycerin solution i.p. twice a week (once on Monday and once on Thursday). The experiments were performed for two weeks. In the chemotherapy group, 100 μl of PBS was administered i.p. into the mice four times a week (once on Sunday, once on Monday, once on Wednesday, once on Thursday) and 100 μl of 3.5 mg/kg cisplatin solution dissolved in PBS was administered i.v. into the mice 30 minutes after the PBS i.p. twice a week (once on Monday and once on Thursday). The experiments were performed for two weeks. In the NO plus chemotherapy group, 100 μl of 0.02 mg/kg nitroglycerin diluted with PBS was administered i.p. into the mice four times a week (once on Sunday, once on Monday, once on Wednesday, once on Thursday) and 100 μl of 3.5 mg/kg cisplatin solution dissolved in PBS was administered i.v. into the mice 30 minutes after the nitroglycerin solution i.p. twice a week (once on Monday and once on Thursday). The experiments were performed for two weeks. Cisplatin and nitroglycerin were obtained from Nippon Kayaku Co., Ltd. (Tokyo, Japan). Measurements of murine tumor volume and mice body weight were performed every two days after the start of injections into the mice.

Results

Figure 3:
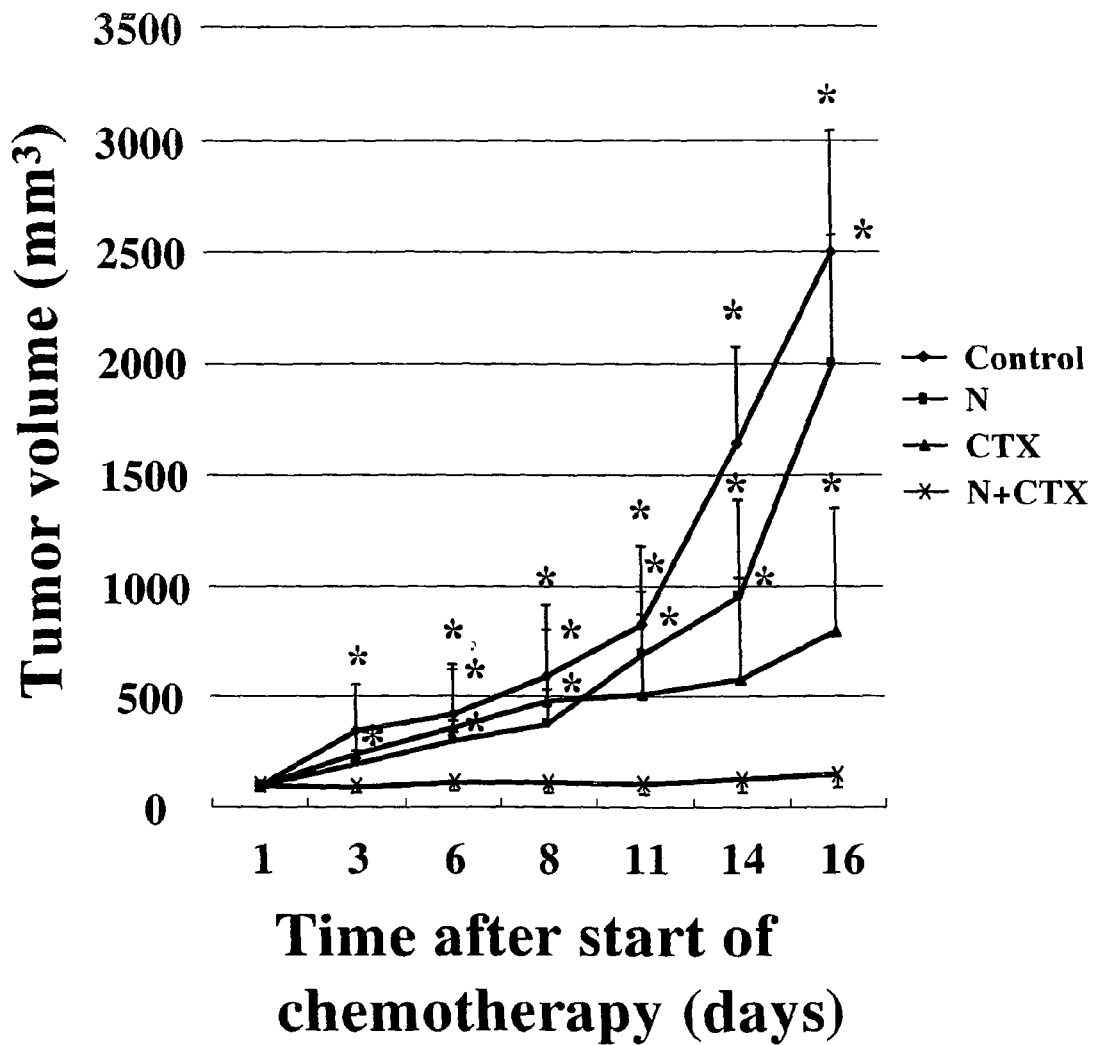
FIG. 3 shows the tumor volume growth curves in colon cancer model (Murine colon cancer cell line; colon 26 cells) in BALB/c mice (Control group, n=6; C, NO donor group, n=6; N, Chemotherapy group, n=6; CTX, and NO plus chemotherapy group, n=6; N+CTX). Tumor volume was calculated as $0.5 \times \{\text{tumor length (mm)}\} \times \{\text{tumor width (mm)}\}^2$. The P value was calculated by student t-test.

The tumor volume growth curve is shown in FIG. 3. Significant diminishing of murine tumor volume was observed after day 6 in the NO plus chemotherapy group compared with that in the chemotherapy group. On the other hand, the NO donor group as well as the control group showed rapid tumor growth compared with that in the chemotherapy group and the NO plus chemotherapy group.

These data suggest that the use of NO donors combined with anticancer agents can enlarge the chance of a new commercial use of NO donors because of their excellent effect on the improvement of chemosensitivity not only in lung cancer but also in colon cancer.

Industrial Applicability

The present invention is able to provide an enhancing agent for effect of anticancer agent for achieving an excellent therapeutic effect on cancer whereby it has an industrial applicability.

The invention claimed is:

1. A method of cancer treatment, comprising:
   administering 1) nitroglycerin at a dosage rate of 1 to 50 mg/day by transdermal administration and 2) a platinum-based anticancer agent to a cancer patient having non-small cell lung cancer or colon cancer.

2. The method of claim 1, wherein the non-small cell lung cancer is adenocarcinoma.

3. The method of claim 1, wherein administration of a course of chemotherapy with the platinum-based anticancer agent begins after the first administration of the nitroglycerin.

4. The method of claim 3, wherein the nitroglycerin is administered at least daily from the first administration of nitroglycerin, to the finish of administration of the platinum-based anticancer agent in the course of chemotherapy.

5. The method of claim 1, wherein at least one anticancer agent selected from the group consisting of antimetabolite, alkylating agent, anticancer antibiotic, microtubule-acting agent, topoisomerase inhibitor and alkaloidal anticancer agent is further administered.

* * * * *